United States Patent [19]

Shaw et al.

[11] 4,256,915

[45] Mar. 17, 1981

[54] PRODUCTION OF ETHYLENICALLY UNSATURATED ALIPHATIC ACIDS

[75] Inventors: Wilfrid G. Shaw, Lyndhurst; David B. Terrill, Bedford, both of Ohio

[73] Assignee: Standard Oil Company, Ohio

[21] Appl. No.: 106,787

[22] Filed: Dec. 26, 1979

[51] Int. Cl.$^3$ .................. C07C 51/25; C07C 57/055
[52] U.S. Cl. .................................. 562/535; 252/467; 252/468; 260/413
[58] Field of Search ............... 562/535; 252/467, 468; 260/413

[56] References Cited

U.S. PATENT DOCUMENTS

| | | | |
|---|---|---|---|
| 3,703,548 | 11/1972 | Honda et al. | 562/535 |
| 4,042,533 | 8/1977 | Shaw et al. | 562/535 |
| 4,051,180 | 9/1977 | Shaw et al. | 562/535 |

*Primary Examiner*—Vivian Garner
*Attorney, Agent, or Firm*—David J. Untener; Herbert D. Knudsen; Larry W. Evans

[57] ABSTRACT

The present invention relates to a process for the production of unsaturated aliphatic acids and the catalyst therefore, by the vapor phase oxidation of the corresponding unsaturated aliphatic aldehydes with molecular oxygen, optionally in the presence of steam, in the presence of an oxidation catalyst consisting of the oxides of the elements molybdenum, vanadium, rhenium, plus at least one of the oxides of magnesium, copper and cadmium.

5 Claims, No Drawings

PRODUCTION OF ETHYLENICALLY UNSATURATED ALIPHATIC ACIDS

BACKGROUND OF THE INVENTION

Catalyst compositions similar to those of the present invention are known for the oxidation of acrolein to acrylic acid. For example, U.S. Pat. No. 3,736,354 discloses catalyst compositions containing molybdenum and vanadium that may be promoted by 17 additional elements, among which are magnesium and copper. Phenium is not disclosed as a possible promoter to these catalysts.

U.S. Pat. No. 3,966,802 discloses a molybdenum-vandium catalyst that may be promoted with alkali metal and optionally tungsten or antimony. The highest single pass yield of acrylic acid shown in this patent is 70.5% without the optional tungsten and 72.8% when tungsten is used as an additional promoter.

U.S. Pat. No. 3,567,773 discloses a molybdenum, vanadium and tungsten catalyst that obtains yields as high as 89% acrylic acid.

Finally, U.S. Pat. No. 4,042,533 discloses a molybdenum, vanadium, tungsten catalyst that may be promoted by one or more of the elements of rhenium and titania. The highest per pass conversion achieved with rhenium catalyst is noted as 87% acrylic acid.

The present invention is based upon the discovery that promoters that have given unacceptable yields in the prior art catalyst, when combined with molybdenum-vanadium catalyst, achieve excellent conversions of aldehydes to acids.

SUMMARY OF THE INVENTION

The present invention relates to an improved process for producing olefinically unsaturated carboxylic acids from the corresponding unsaturated aldehydes and to the catalyst composition utilized therefore. More specifically, the present invention relates to a vapor phase process for producing acrylic acid or methacrylic acid from acrolein and methacrolein, respectively, by oxidation of the unsaturated aldehydes with molecular oxygen, optionally in the presence of steam, and in the presence of an oxidation catalyst having the empirical formula $$Mo_aV_bRe_cX_dO_e$$

wherein X is one or more of the elements selected from the group consisting of magnesium, copper and cadmium, and
wherein the number of each element present is represented by a–d,
wherein
a is a number from 8–16;
b is a number from 0.5 to 5;
c is a number from 0.01 to 5;
d is a number from 0.01 to 5; and
e is a number that satisfies the valence requirements of the other elements present.

Preferred catalysts are those wherein a is 12; b is between 0.5 and 3; c is between 0.01 and 1; and d is from 0.01 and 1. The elements are present in these catalytic compositions in the form of their oxides or oxide complexes.

In addition to the active catalytic ingredient, the catalyst of the invention may contain a support material. Suitable support materials include silica, alumina, zirconia, silicon carbide and the like. A preferred support material is Alundum.

The catalysts of this invention are highly effective for oxidation reactions. Preferred among these reactions is the production of unsaturated acids from the corresponding unsaturated aldehydes, and more specifically the catalysts of the invention are capable of very selectively oxidizing acrolein to acrylic acid.

The oxidation of unsaturated aldehydes to obtain the corresponding acid is well known in the art. Basically the invention, with respect to the process, is the use of the new catalyst within the parameters of the known art process.

The known process involves the contacting of the unsaturated aldehyde with molecular oxygen in the presence of steam at a temperature of about 200° to about 500° C. The ratio of the reactants may vary widely, with molar ratios of molecular oxygen to aldehyde of about 0.5 to about 5 normally being employed. Molecular oxygen is most conveniently added as air. The amount of steam may vary widely from the small amount generated in the reaction to 20 or more moles of steam per mole of aldehyde.

The reaction may be conducted in a fixed-bed or fluid-bed reactor or forms thereof, using atmospheric, superatmospheric or subatmospheric pressure. The apparent contact time may vary considerably, with contact times of a fraction of a second to 20 seconds or more normally being employed.

As noted above, catalysts very similar to the catalyst of the invention are known. See for example U.S. Pat. No. 4,042,533, and thus catalysts of this general type can readily be prepared by persons of ordinary skill in the art.

Normally, the catalysts of the invention are prepared by mixing the catalyst ingredients in the proper proportions in an aqueous mixture, drying the resulting aqueous slurry and calcining the product. The ingredients going into the preparation of the catalyst can be the oxides, halides, nitrates, acetates or other salts of the particular compound added. If the support is used, the material comprising the support can be incorporated into the catalyst along with the other ingredients, or the catalyst can be coated upon a suitable support material. After the catalyst ingredients have been combined to form an aqueous slurry, the slurry is evaporated to dryness, and the dried solid obtained is heated in the presence of air at temperatures between about 200° and 600° C. This calcination can take place outside of the catalytic reactor or an in situ activation can be utilized.

SPECIFIC EMBODIMENTS

Catalyst Preparation

The catalysts of Comparative Examples A through C and Examples 1–5 were prepared according to the following procedure.

EXAMPLE 1

Catalyst $Mo_{12}V_3Re_{.5}Mg_{.2}O_{45.4}$

To 200 cc of hot distilled water were added 4.94 grams of ammonium metavanadate, 29.85 grams ammonium heptamolybdate, 1.89 grams $NH_4ReO_4$ and 0.604 grams $Mg(C_3H_3O_2)_2 \cdot 4H_2O$. After all the chemicals were in solution, 0.75 grams hydrazine hydrate were added. The solution was then evaporated to near dryness with continual stirring and heating on a hot plate.

The contents were then dried at 110°-120° C. overnight.

The dried material was crushed and ground to pass through a 50 mesh screen. 15 grams of this material was then coated on 3/16" Alundum spheres to achieve a 20 wt.% coating on the spheres. The coated spheres were then dried at 110° C. for 16 hrs, and then activated by heat treating at 370° C. for 2 hrs.

The catalysts of all the examples were placed in a 20 ml fixed-bed reactor. The reactor was heated in a split block furnace. The reactor feed was a mixture of acrolein/air/N$_2$/steam in the molar ratio of 1/8.5/2.5/6. The reaction was conducted at atmospheric pressure, and the apparent contact time was 2.5 seconds. The reaction temperatures employed and the conversions obtained are summarized in the table as follows:

$$\text{Percent Conversion} = \frac{\text{Moles of acrolein reacted}}{\text{Moles of acrolein fed}} \times 100$$

$$\text{Percent Single Pass Yield} = \frac{\text{Moles of product recovered}}{\text{Moles of acrolein fed}} \times 100$$

COMPARATIVE EXAMPLES A-C

Comparative Example A shows that a molybdenum vanadium catalyst without any promoters achieves less than 50% total conversion with only 34% single pass yield to acrylic acid. When rhenium is added to the above catalyst as shown in Comparative Example B, both the total conversion and the single pass yield decreases. Finally, Comparative Example C shows that when magnesium is added to a molybdenum-vanadium catalyst, there is a minor increase in total conversion and single pass yield, but the results are still extremely low.

EXAMPLES 1-2

Rhenium and Magnesium Containing Catalysts

As shown in the Table, when both rhenium and magnesium are used to promote a molybdenum-vanadium catalyst, a totally unexpected result is obtained. The total conversion of acrolein is over 97%, with single pass yields to acrylic acid as high as 92%.

EXAMPLES 3-4

Copper and Cadmium Promoted Catalysts

As shown in the Table, both copper and cadmium achieve high conversions of acrolein with very acceptable single pass yields to acrylic acid when combined with rhenium.

EXAMPLE 5

Double Promoted Catalysts

Example 5 shows the effect of promoting a rhenium-vanadium-molybdenum catalyst with both magnesium and copper. Utilizing this combination, single pass yields to acrylic acid as high as 92% were obtained.

TABLE

Oxidation of Acrolein to Acrylic Acid

| Example | Catalyst Comp. | Temp. °C. | % Copy Acrolein | Single Pass Yield Acrylic Acid | Acetic Acid |
|---|---|---|---|---|---|
| Comp. A | Mo$_{12}$V$_3$O$_{43.5}$ | 356 | 47.6 | 34.2 | 0.9 |
| Comp. B | Mo$_{12}$V$_3$Re$_{.5}$O$_{45.2}$ | 346 | 36.8 | 28.6 | 0.7 |
| Comp. C | Mo$_{12}$V$_3$Mg$_{.2}$O$_{43.7}$ | 359 | 57.6 | 47.4 | 0.8 |
| 1 | Mo$_{12}$V$_3$Re$_{.5}$Mg$_{.2}$O$_{45.4}$ | 309 | 99.0 | 92.3 | 1.3 |
| 2 | Mo$_{12}$V$_3$Re$_{.75}$Mg$_{.3}$O$_{46.4}$ | 333 | 97.6 | 86.2 | 2.4 |
| 3 | Mo$_{12}$V$_3$Re$_{.5}$Cu$_{.5}$O$_{45.8}$ | 343 | 94.2 | 80.6 | 2.1 |
| 4 | Mo$_{12}$V$_3$Re$_{.5}$Cd$_{.2}$O$_{45.4}$ | 372 | 91.2 | 71.2 | 4.2 |
| 5 | Mo$_{12}$V$_3$Re$_{.5}$Mg$_{.2}$Cu$_{.1}$O$_{45.4}$ | 310 | 98.9 | 92.6 | 1.6 |

We claim:

1. The process for the production of olefinically unsaturated aliphatic acids by vapor phase catalytic oxidation of corresponding olefinically unsaturated aliphatic aldehydes with molecular oxygen, said reaction occurring over an oxidation catalyst represented by the following formula:

$$Mo_aV_bRe_cX_dO_e$$

wherein
X is one or more of the elements selected from the group consisting of magnesium, copper and cadmium, and wherein
the number of each element present is represented by a-d;

wherein
a is a number from 8-16;
b is a number from 0.5 to 5;
c is a number from 0.01 to 5;
d is a number from 0.01 to 5; and
e is a number that satisfies the valence requirements of the other elements present.

2. The process of claim 1 wherein a is 12; b is a number from 0.5 to 3; c is a number from 0.01 to 1; d is a number from 0.01 to 1; and e is a number that satisfies the valence requirements of the other elements present.

3. The process of claim 1 wherein the unsaturated aliphatic acid is acrylic acid and the unsaturated aldehyde is acrolein.

4. The process of claim 1 wherein X is magnesium.

5. The process of claim 1 wherein X is magnesium and copper.

* * * * *